(12) United States Patent
Ellis et al.

(10) Patent No.: US 8,070,957 B2
(45) Date of Patent: *Dec. 6, 2011

(54) FLASH CHROMATOGRAPHY CARTRIDGE

(75) Inventors: Samuel A. Ellis, San Diego, CA (US); Jeffrey L. Harlan, Corona, CA (US)

(73) Assignee: Scientific Plastic Products, Inc., Oceanside, CA (US)

( * ) Notice: Subject to any disclaimer, the term of this patent is extended or adjusted under 35 U.S.C. 154(b) by 736 days.

This patent is subject to a terminal disclaimer.

(21) Appl. No.: 12/152,166

(22) Filed: May 13, 2008

(65) Prior Publication Data
US 2008/0210616 A1 Sep. 4, 2008

Related U.S. Application Data

(60) Continuation of application No. 11/476,292, filed on Jun. 28, 2006, now Pat. No. 7,410,571, which is a division of application No. 10/842,288, filed on May 10, 2004, now Pat. No. 7,138,061.

(51) Int. Cl.
*B01D 15/08* (2006.01)
(52) U.S. Cl. .................................. 210/656; 210/198.2
(58) Field of Classification Search .................. 210/635, 210/656, 659, 198.2, 232, 450; 96/101
See application file for complete search history.

(56) References Cited

U.S. PATENT DOCUMENTS

| | | |
|---|---|---|
| 3,433,380 A | 3/1969 | Kawchitch |
| 3,435,975 A | 4/1969 | Weigand |
| 3,441,161 A | 4/1969 | Van Baarn |
| 3,595,418 A | 7/1971 | Adcock et al. |
| 3,682,315 A | 8/1972 | Haller |
| 3,692,669 A | 9/1972 | Bauman |
| 3,791,522 A | 2/1974 | Eisenbeiss et al. |
| 3,901,404 A | 8/1975 | Feldman |
| 4,084,718 A | 4/1978 | Wadsworth |
| 4,131,547 A | 12/1978 | Michel |
| 4,143,785 A | 3/1979 | Ferrell |
| 4,283,280 A | 8/1981 | Brownlee |
| 4,309,286 A | 1/1982 | Lenihan, Jr. et al. |
| 4,322,012 A | 3/1982 | Conti |
| 4,341,635 A | 7/1982 | Golias |

(Continued)

FOREIGN PATENT DOCUMENTS
WO  WO 02/42171  5/2002

OTHER PUBLICATIONS

Order Granting Request for Reexamination of Patent No. 7,410,571 (Reexam. Cont. No. 95/000,496), dated Nov. 25, 2009.

(Continued)

*Primary Examiner* — Ernest G Therkorn
(74) *Attorney, Agent, or Firm* — David M. Quinlan, P.C.

(57) ABSTRACT

A low pressure liquid chromatographic cartridge is provided having a tubular polymer container adapted to receive a chromatographic packing material. The container has an outlet port located at a downstream end of the container and container threads formed on an upstream end of the container. A polymer cap having cap threads located on the cap threadingly engage the container threads. An inlet port is located on an upstream end of the cap. A resilient fluid tight seal is interposed between the polymer cap and container suitable for use in low pressure liquid chromatography. A locking tab on a skirt of the cap engages a recess on the container when the seal engages the cap and container to lock the cap in position relative to the container.

2 Claims, 5 Drawing Sheets

U.S. PATENT DOCUMENTS

| | | | |
|---|---|---|---|
| 4,354,932 | A | 10/1982 | McNeil |
| 4,392,579 | A | 7/1983 | Uhlig et al. |
| 4,457,846 | A | 7/1984 | Munk |
| 4,496,461 | A | 1/1985 | Leeke et al. |
| 4,582,608 | A | 4/1986 | Ritacco |
| 4,662,529 | A | 5/1987 | Moore |
| 4,670,141 | A | 6/1987 | Shackelford et al. |
| 4,692,243 | A | 9/1987 | Porsch |
| 4,758,340 | A | 7/1988 | Marchand et al. |
| 4,856,668 | A | 8/1989 | Pfefferkorn et al. |
| 4,863,610 | A | 9/1989 | Campbell |
| 4,888,112 | A | 12/1989 | Kronwald |
| 4,894,152 | A | 1/1990 | Colvin |
| 4,927,531 | A | 5/1990 | Sakamoto et al. |
| 4,988,127 | A | 1/1991 | Cartensen |
| 5,100,013 | A | 3/1992 | Strassheimer |
| 5,167,810 | A | 12/1992 | Vassarotti et al. |
| 5,188,730 | A | 2/1993 | Kronwald |
| 5,238,556 | A | 8/1993 | Shirkhan |
| 5,297,688 | A | 3/1994 | Beck et al. |
| 5,411,157 | A | 5/1995 | King, II |
| 5,462,659 | A | 10/1995 | Saxena et al. |
| 5,601,708 | A | 2/1997 | Leavesley |
| 5,667,676 | A | 9/1997 | Alaska |
| 5,693,223 | A | 12/1997 | Yamada et al. |
| 5,714,074 | A | 2/1998 | Karlsson et al. |
| 6,068,766 | A | 5/2000 | Van Davelaar |
| 6,132,605 | A | 10/2000 | Leavesley et al. |
| 6,139,733 | A | 10/2000 | Hargro et al. |
| 6,171,486 | B1 | 1/2001 | Green et al. |
| 6,171,502 | B1 | 1/2001 | Mueller |
| 6,221,252 | B1 | 4/2001 | Hargro et al. |
| 6,260,723 | B1 | 7/2001 | Bergholtz |
| 6,280,616 | B1 | 8/2001 | Pettersson |
| 6,294,087 | B1 | 9/2001 | Hargro et al. |
| 6,352,266 | B1 | 3/2002 | Rigoli |
| 6,387,256 | B1 | 5/2002 | Tuvirn |
| 6,436,284 | B1 | 8/2002 | Leavesley et al. |
| 6,444,122 | B1 | 9/2002 | Van Davelaar |
| 6,457,905 | B1 | 10/2002 | Nickell |
| 6,491,175 | B1 | 12/2002 | Taha |
| 6,565,745 | B2 | 5/2003 | Hodgin et al. |
| 6,695,161 | B2 | 2/2004 | Kano et al. |
| 6,702,133 | B1 | 3/2004 | Shenkar |
| 6,783,673 | B2 | 8/2004 | Horsman et al. |
| 6,802,968 | B2 | 10/2004 | Leavesley et al. |
| 6,949,194 | B2 | 9/2005 | Hodgin et al. |
| 7,008,541 | B2 | 3/2006 | Hodgin et al. |
| 7,018,365 | B2 | 3/2006 | Strauss et al. |
| 7,138,061 | B2 | 11/2006 | Ellis et al. |
| 7,381,327 | B2 | 6/2008 | Ellis et al. |
| 7,410,571 | B2 | 8/2008 | Ellis et al. |
| 2003/0062330 | A1 | 4/2003 | Scalese |
| 2003/0102266 | A1 | 6/2003 | Ritacco |
| 2006/0011532 | A1 | 1/2006 | Van Davelaar et al. |
| 2007/0068861 | A1 | 3/2007 | Ellis et al. |

OTHER PUBLICATIONS

Office Action dated Nov. 25, 2009, in Reexam. Cont. No. 95/000,496.
Response to Office Action (by the patent owner), dated Jan. 27, 2010, including Exhibits A-E thereto, in Reexam. Cont. No. 95/000,495.
Comments to Patent Owner's Response to Office Action Regarding Reexamination of U.S. Patent No. 7,381,327 (by Biotage AB), dated Feb. 25, 2010, including Declarations of William H. Pearson and Juha Esala (with exhibits), in Reexam. Cont. No. 95/000,495.
Response to Office Action (by the patent owner), dated Jan. 25, 2010, including Exhibit A thereto, in Reexam. Cont. No. 95/000,496.
Comments to Patent Owner's Response to Office Action Regarding Reexamination of U.S. Patent No. 7,410,571 (by Biotage AB), dated Feb. 24, 2010, including Declarations of William H. Pearson and Juha Esala (with exhibits), in Reexam. Cont. No. 95/000,496.
Responie to Office Action (by the patent owner), dated Jan. 27, 2010, including Exhibit A thereto, in Reexam. Cont. No. 95/000,497.
Comments to Patent Owner's Response to Office Action Regarding Reexamination of U.S: Patent No. 7;138,061 (by Biotage AB), dated Feb. 25, 2010, including Declarations of William H. Pearson and Juha Esala (with exhibits), in Reexam. Cont. No. 95/000,497.
Exhibits 14-25 to Request for Inter Partes Reexamination of U.S. Patent No. 7,381,327, dated Aug. 21, 2009 (Reexam. Cont. No. 95/000,495).
Exhibits 13-22 to Request for Inter Partes Reexamination of U.S. Patent No. 7,410,571, dated Aug. 21, 2009 (Reexam. Cont. No. 95/000,496).
Exhibits 10-25 to Request for Inter Partes Reexamination of U.S. Patent No. 7,138,061, dated Aug. 21, 2009 (Reexam. Cont. No. 95/000,497).
Still, Clark, et al., "Rapid Chromatographic Technique for Preparative Separations with Moderate Resolutions," J. Org. Chem., vol. 44, Nov. 14, 1978, pp. 2923-2925.
Office action closing prosecution in Reexam. Cont. No. 95/000,495 (of Patent No. 7,381,327), dated Aug. 28, 2010.
Response to Office Action (by the patent owner), dated Nov. 17, 2010, including Exhibits A-C (with exhibits), in Reexam. Cont. No. 95/000,495.
Requester's Comments to Office Action Closing Prosecution and Patent Owner's Response Regarding Reexamination of U.S. Patent No. 7,381,327 (by Biotage AB), dated Dec. 17, 2010, including Second Declarations of William H. Pearson and Juha Esala, in Reexam. Cont. No. 95/000,495.
Right of Appeal Notice in Reexam. Cont. No. 95/000,495, dated Mar. 3, 2011.
Office action closing prosecution in Reexam. Cont. No. 95/000,496 (of Patent No. 7,410,571), dated Oct. 2, 2010.
Response to Office Action (by the patent owner), dated Nov. 17, 2010, including Exhibits A-C (with exhibits), in Reexam. Cont. No. 95/000,496.
Requester's Comments to Office Action Closing Prosecution and Patent Owner's Response Regarding Reexamination of U.S. Patent No. 7,410,571 (by Biotage AB), dated Dec. 17, 2010, including Second Declarations of William H. Pearson and Juha Esala, in Reexam. Cont. No. 95/000,496.
Office action closing prosecution in Reexam. Cont. No. 95/000,497 (of Patent No. 7,138,061), dated Jan. 18, 2011.
Response to Office Action (by the patent owner), dated Mar. 17, 2011, including Exhibits A-C (with exhibits), in Reexam. Cont. No. 95/000,497.
Requester's Comments to Office Action Closing Prosecution and Patent Owner's Response Regarding Reexamination of U.S. Patent No. 7,138,061 (by Biotage AB), dated Apr. 15, 2011, including Second Declarations of William H. Pearson and Juha Esala (with exhibit), in Reexam. Cont. No. 95/000,497.
Right of Appeal Notice in Reexam. Cont.I No. 95/000,497, dated May 5, 2011.
Request for Re-examination of U.S. Patent No. 7,138,061, Requester's Docket No. 086679-0103. Re-examination Control No. 95/000,497.
Request for Re-examination of U.S. Patent No. 7,381, 327, Requester's Docket No. 086679-0104. Re-examination Control No. 95/000,495.
• Request for Re-examination of U.S. Patent No. 7,410,571, Requester's Docket No. 086679-0105. Re-examination Control No. 95/000,496.
Reply to Notice of Failure to Comply with Re-examination filing requirements for U.S. Patent No. 7,410,571. Re-examination Control No. 95/000,496.
Order granting Request for Re-examination of Patent No. 7,381,327 Control No. 95/000,495.
Office Action involving claims 1-20 for the Re-examination of Patent No. 7,381,327, Control No. 95/000,495.
Order granting Request for Re-examination of Patent No. 7,138,061 Control No. 95/000,497.
Office Action involving claims 1-22 for the Re-examination of Patent No. 7,138,061 Control No. 95/000,497.
Appeal Brief (by the patent owner) in Reexam. Cont. No. 95/000,495 (of Patent No. 7,381,327), dated Jun. 6, 2011.
Respondent Brief in Inter Partes Reexamination (by the requester) in Reexam. Cont. No. 95/000,495, dated Jul. 6, 2011.

Appeal Brief (by the patent owner) in Reexam. Cont. No. 95/000,497 (of Patent No. 7,318,061), dated Aug. 8, 2011.

Right of Appeal Notice in Reexam. Cont. No. 95/000,497, dated Sep. 2, 2011.

Respondent Brief in Inter Partes Reexamination (by the requester) in Reexam. Cont. No. 95/000,497, dated Sep. 8, 2011.

Revised Appeal Brief (by the patent owner) in Reexam. Cont. No. 95/000,497, dated Sep. 16, 2011.

Appeal Brief (by the patent owner), dated Jun. 6, 2011, in Reexam. Cont. No. 95/000,495 (of Patent No. 7,381,327).

Respondent Brief in Inter Partes Reexamination (by the requester Biotage AB), dated Jul. 6, 2011, including Exhibit Y, in Reexam. Cont. No. 95/000,495.

Innovative Tools for Molecular and Cell Biology, MoBiTec GmbH, GOItIngen, Germany (1999).

Innovative Tools for Molecular and Cell Biology, MoBiTec GmbH, Göttingen, Germany (1999).

US 8,070,957 B2

FLASH CHROMATOGRAPHY CARTRIDGE

RELATED U.S. APPLICATION DATA

The present application is a continuation of U.S. application Ser. No. 11/476,292, filed Jun. 28, 2006, and issued as U.S. Pat. No. 7,410,571, which in turn was a division divisional of U.S. application Ser. No. 10/842,288, filed May 10, 2004, and issued as U.S. Pat. No. 7,138,061, the complete contents of which related applications are hereby incorporated by reference.

BACKGROUND OF THE INVENTION

This invention relates to method and apparatus involving cartridges for use in flash chromatography and low pressure liquid chromatography equipment.

Chromatographic analysis passes fluids through columns containing specially treated sorbent which allows the chemicals in the fluid to be eluted at different times and thus form separated peaks on a chromatogram. In order to prepare or clean up the fluid being analyzed the fluid is often passed through a sorbent under pressure. Further, for low pressure liquid chromatography (LPLC) or flash chromatography the fluid may be passed through a sorbent at a pressure of 20-100 psi. This operating pressure is sufficiently high that these cartridges, which have relative large diameter bodies leak at the seams. Threaded connections are thus not used to form the body when the body is made of polymers. Thus, these cartridges are traditionally made of plastic and have sonically welded ends. But even that welded construction will leak if there are defects in the welds. That welded construction and the accompanying manufacturing and material costs cause in undesirably high costs, especially as the cartridges must be either discarded, or must under go extensive and thorough cleaning after a single use, or at most after a few uses with similar fluids. There is thus a need for a low cost, disposable cartridge.

Further, the welded construction requires the chromatographic packing material be placed in the cartridge before it is welded, or it requires careful packing of the column under pressure, both of which limit the usefulness of the cartridge and increase its cost.

Recently one company has introduced a disposable cartridge made of molded polypropylene having an end fitting that uses openings in a number of cantilever members to engage detent members which fit into the openings to create an interference fit to snap-lock the end fitting onto the cartridge. This is described in U.S. Pat. No. 6,565,745. But this interference fit is created at the factory and again creates a cartridge that docs not allow the user to easily vary the contents of the cartridge. There is thus a need for a cartridge that can be sealed to function under LPLC pressures but which allows the user to access the inside of the cartridge before it is sealed.

In LPLC the fluid sample is sometimes prepared by passing it through one or more cartridges of different material, each of which has a different sorbent to clean the fluid of particular undesirable materials or chemicals. Because the fluid sample can vary, a wide variety of cartridges with different sorbents sealed in the cartridges must be maintained. Further, the removal and reconnection of these various cartridges is cumbersome and time consuming, and the cost of each cartridge is expensive. There is thus a need for a way to reduce the complexity and cost of using different sorbents.

Sometimes a Y fitting is used to inject one or more fluids into the LPLC cartridge. The connection and use of these Y fittings is cumbersome. Further, the fitting must be either discarded or cleaned after each use. There is thus a need for a better and less expensive way to introduce fluid or materials into the cartridge.

SUMMARY

A low pressure liquid chromatographic cartridge is provided having a tubular polymer container adapted to receive a chromatographic packing material. The container has an outlet port located at a downstream end of the container and configured for connecting to chromatographic equipment during use of the cartridge. Container threads are formed on an upstream end of the container. A polymer cap has cap threads located on the cap to threadingly engage the container threads. The cap also has an inlet port located on an upstream end of the container. The port is configured for connecting to chromatographic equipment during use of the cartridge. A resilient fluid tight seal is interposed between the cap and container suitable for use in low pressure liquid chromatography. A locking tab is provided on a skirt of the cap and is located and configured to engage a recess on the container when the seal engages the cap and container. The locking tab locks the cap in position relative to the container.

In further variations the seal comprises a resilient ring extending from a top of the cap with the seal being located and sized to engage a lip of the container. Preferably a fluid dispenser is interposed between the container and the cap. The dispenser has a plurality of fluid outlets located across a substantial portion of a cross-section of the container to dispense fluid from the inlet of the cap over the cross-section. The fluid dispenser preferably takes the form of a dish having a plurality of holes extending through the dish, so as to place the inlet and the outlet in fluid communication. Moreover, the dish preferably, but optionally has a rim placed between the cap and the container. In further embodiments the locking tab extends parallel to a longitudinal axis of the container and extends from a distal end of a skirt of the cap. Further, the inlet can take the form of a tube threadingly engaging one of the cap or container, with the tube having a threaded exterior distal end located on an exterior of the engaged one of the cap or container. Advantageously the seal and lip abut at an inclined angle with the seal extending inward toward a longitudinal axis of the container and cap. Moreover, the seal preferably joins the top of the cap at a corner which encircles a longitudinal axis of the container. Still further, the fluid dispenser has a periphery located in that corner. Preferably chromatographic packing material is placed in the cartridge by the user before the cap is locked onto the container. Preferably, but optionally, the material to be analyzed is also placed in the cartridge by the user before the cap is locked onto the container. This allows the user to custom select and place any of a plurality of different chromatographic packing materials in the container.

In a further embodiment there is provided a low pressure liquid chromatography cartridge having a tubular container adapted to receive a chromatographic packing material. The container has an outlet port located at a downstream end of the container and configured for use with chromatographic equipment during use of the cartridge. The container also has container threads formed on an upstream end of the container. A cap is provided with an inlet port located on an upstream end of the cap, with port being configured for use with chromatographic equipment during use of the cartridge. The cap also has cap threads located on the cap to threadingly engage the container threads. Locking means on the container and cap prevent manual removal of the cap. Resilient sealing means are provided for sealing the cap to the container when a user places the cap on the container and engages the locking means.

In still further variations, the cartridge has means for distributing fluid from the inlet port over a cross-section area of the container during use of the cartridge. Moreover, chromatographic packing material and materials to be analyzed can be placed in the container by the user of the cartridge before the locking means are locked.

There is also provided a method for a user to perform low pressure liquid chromatography. The method includes placing at least one chromatographic packing material in a tubular container which has an outlet port located at a downstream end of the container. The outlet is again configured for use with chromatographic equipment. Container threads are formed on an upstream end of the container. The method includes threadingly engaging threads on a cap with the container threads. The cap is also provided with an inlet port on an upstream end of the cap. The method further includes sealing the cap to the container by tightening the threads and engaging a seal between the cap and the container. The seal provides a fluid tight seal below about 100 psi suitable for LPLC use.

In further variations the method includes locking the cap to the container. A still further variation includes connecting the inlet to a source of fluid for chromatographic analysis; and distributing the fluid from the inlet over a cross-section area of the container. Moreover, distributing step preferably, but optionally includes collecting the fluid in a fluid dispenser having a wall with a plurality of holes spread across the cross-section and passing the fluid through those holes. Inclining the surface with the holes toward a central longitudinal axis of the fluid dispenser which also passes through the fluid dispenser is also a preferred variation. In a still further variation the distributing step is performed by a fluid dispenser with a periphery that is interposed between the cap and the container.

BRIEF DESCRIPTION OF THE DRAWINGS

These and other features and advantages of the invention will be better understood by reference to the following drawings in which like numbers refer to like parts throughout, and in which.

DETAILED DESCRIPTION

Figure 1:
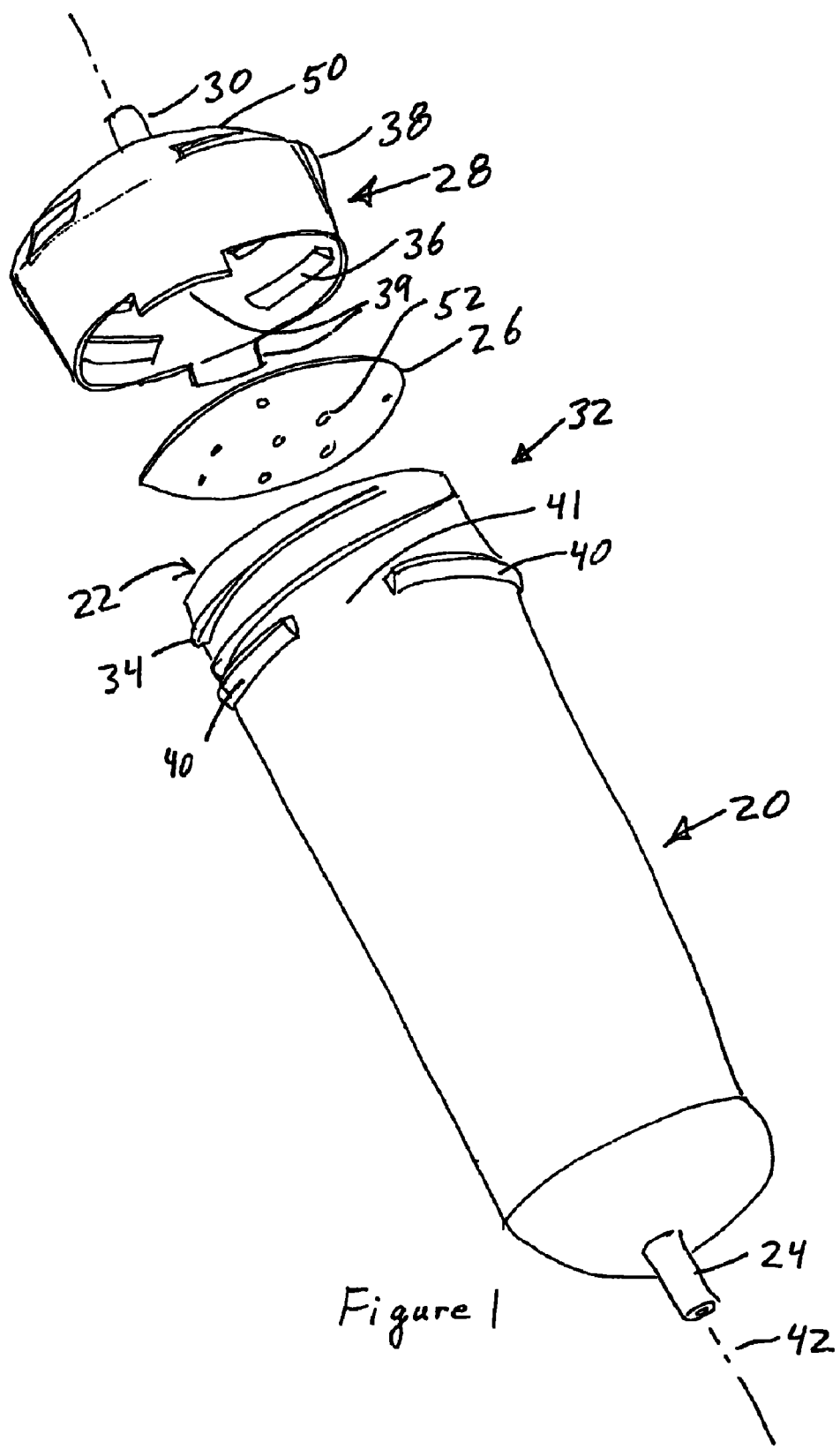
FIG. 1 is a perspective view of a first embodiment of a cartridge with a screw cap.
Figure 2:
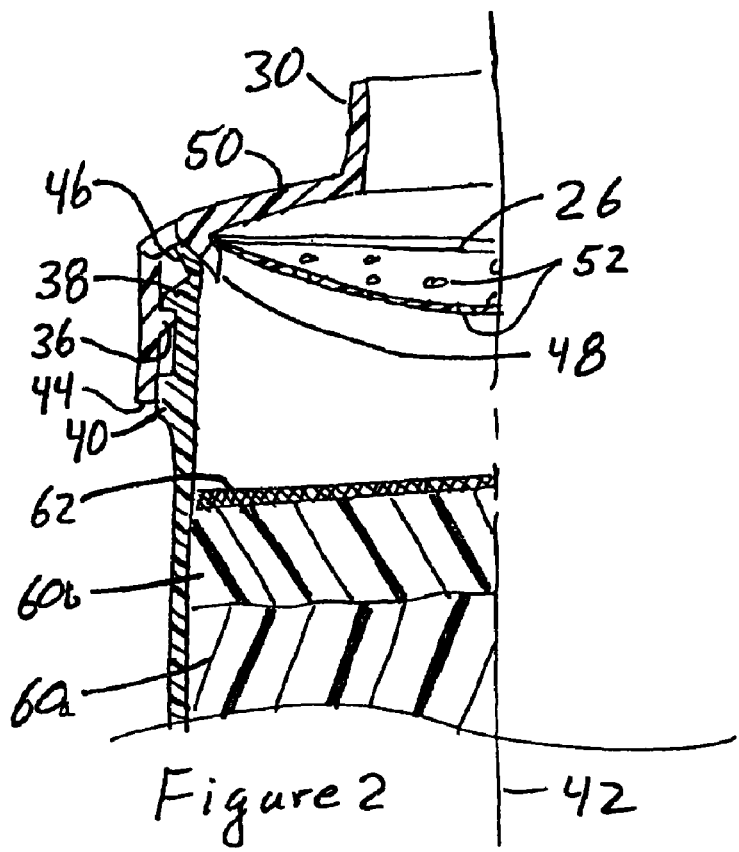
FIG. 2 is a partial sectional view of the juncture of the cap and cartridge of FIG. 1.
Figure 7:
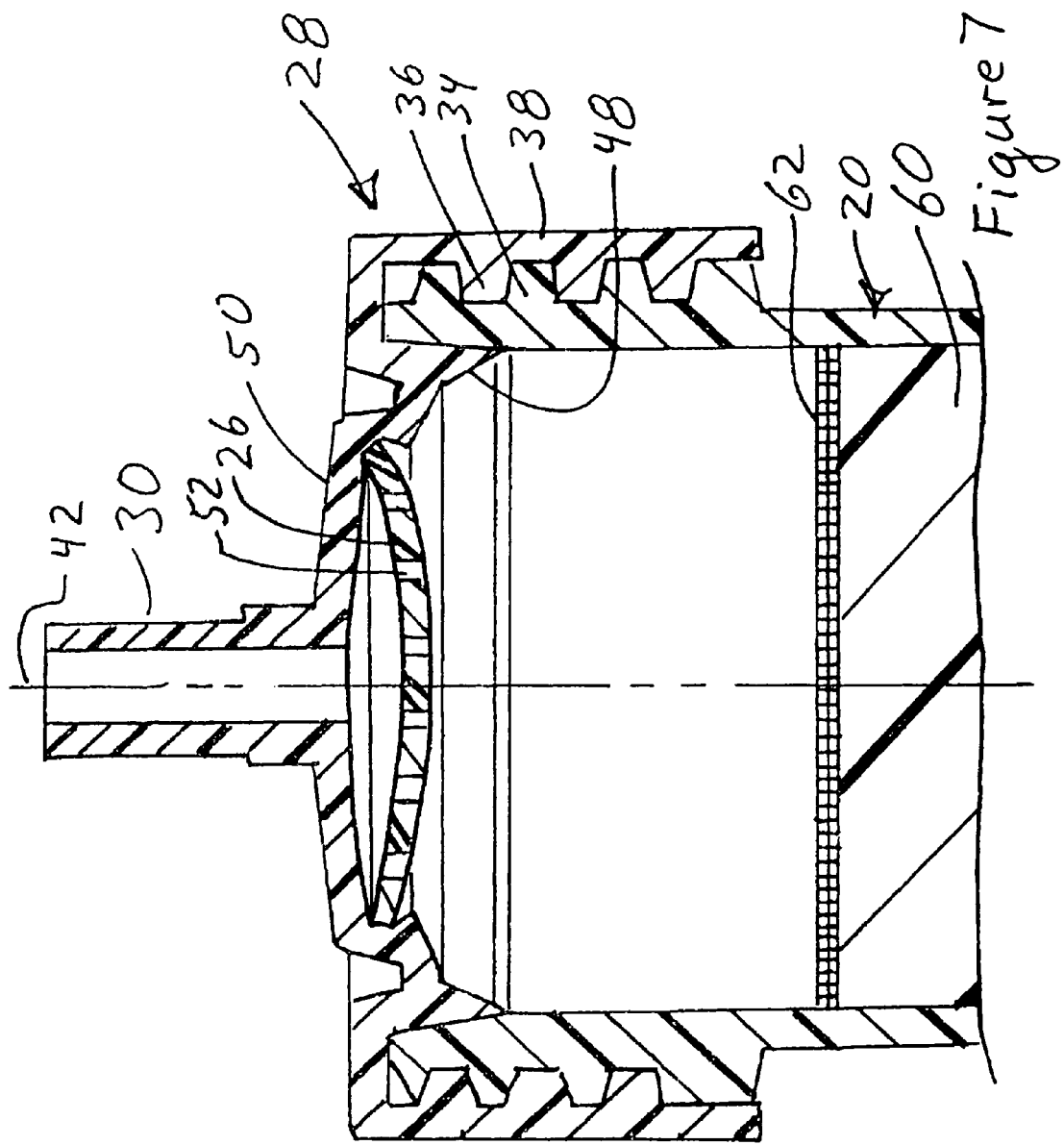
FIG. 7 is a partial sectional view of a further embodiment of the connection of the cap and the container of FIG. 1.

Referring to FIGS. 1-2 and 7, a cartridge is provided comprising tubular container 20 and cap 28 with inlet and outlet ports 24, and 30, respectively. The container 20 has an open end 22 at and upstream or proximal end, and an outlet port 24 at a downstream or distal end. A fluid dispenser 26 is placed in or upstream of the open end 22 and a cap 28 is fastened over the open end 22 and fluid dispenser. An inlet port 30 is provided on the cap 28. A locking mechanism 32 is placed on one or both of the container 20 and cap 28 to hold the cap to the container. A seal 48 between the cap 28 and container 20 is held in fluid tight compression by mating threads 32, 34 and the locking mechanism 32.

In use, the inlet 30 is placed in fluid communication with a source of fluid to be processed in a low pressure liquid chromatography (LPLC) or flash chromatography process. Processing or filtering media is placed in the container 20. The sample fluid to be tested is passed through the media in the container, and the resulting fluid is removed from the outlet port 24 for further processing or other treatment or analysis. Preferably, but optionally, the outlet port 24 is placed in fluid communication with the LPLC equipment or other chromatographic equipment for the processing or treatment. Advantageously the downstream or distal end of the container 20 is slightly curved or domed or inclined so the fluid being processed is funneled toward the outlet 24.

In more detail, the locking mechanism 32 can advantageously, but optionally take the form of mating threads on the container 20 and the cap 28. FIG. 1 shows external threads 34 on the container mating with internal threads 36 on a skirt 38 of the cap 28. But the container threads 24 could be internal threads and the cap threads 36 could be external threads. The threads can 34, 36 be single lead, or multiple lead. The threads 34, 36 can be continuous or segmented.

Preferably, but optionally, a lip or flange 40 extends outward around the outer circumference of the container 20 adjacent the trailing end of the threads. Preferably, one or more gaps or spaces or recesses 41 are formed in the flange 40. As used herein, the leading end of the threads refers to the ends that first engage the mating threads, and the trailing end refers to the last to engage end of the threads. The outward direction means away from the longitudinal axis 42 of the container 20.

Referring to FIG. 2, the polymer cap 28 is sealed to the polymer container 20 sufficiently to allow flash chromatography up to about 100 psi. A lip 44 is formed on the distal edge of the skirt 38 of the cap 28 so the lip 38 abuts the flange 40 on the container to limit the tightening of the cap on the container 20, and to help seal the cap to the container. A locking tab 39 extends from the skirt 28 along the direction of axis 42. The locking tab 39 is sized and shaped to fit into one of the recesses 41 on the flange 40. Thus, when the cap 28 is threaded onto the container 20 by threads 34, 36, the tabs 39 advance axially along axis 42 and fit into the recesses 41 to lock the cap from further rotation, and to lock the cap from unscrewing and the accompanying leaking. The tabs could be located on the container and the recesses on the cap.

Advantageously the locking tabs 39 are configured so the shape matches that of the flange 40, making it difficult to manually grab the tabs 39 and manipulate them to unscrew the cap 28. Advantageously, but optionally, the distal or downstream edge of the locking tab 39 tapers toward the axis 42 and that helps remove defined edges of sufficient size that the edge can be manually grabbed, and that helps avoid unlocking the cap. The locking tabs 39 thus provide means for preventing manual removal of the cap.

A shaped lip 46 is also preferably, but optionally placed around the opening 22 on the proximal or upstream end of the container 20. The shaped lip 46 is shown as inclined outward at an angle of about 30° from a line parallel to axis 42. The container lip 46 abuts a sealing surface 48 on the cap 28 to provide a fluid tight seal. Different angles and lip shapes could be used, especially if different types of seals are used.

The cap sealing surface 48 is shown as comprising an annular seal depending from the inside of the cap 28. The sealing surface 48 is shown as connected to a top wall 50 adjacent the juncture of the top wall 50 with the side walls or skirt 38 of the cap 28. The top wall 50 is preferably, but optionally slightly domed or slightly curved outward. The sealing surface 46 is advantageously a thin walled ring, and preferably, but optionally has a slight conical shape narrowing toward the downstream end of the cap 28 and inward toward the axis 42. The cap sealing surface 48 thus preferably has a larger diameter at the upstream or proximal end where it fastens to the cap 28, and has a smaller diameter, open end located downstream and inward of the upper end to form a cone with the smaller end facing downstream.

Preferably, but optionally, the cap sealing surface 48 is integrally molded with the cap 28, although a two part assembly is also believed suitable. Referring to FIGS. 1-2, a series of rectangular openings appear near the juncture of the skirt 38 and the top of the cap 28 and these openings allow mold slides to pass through the cap to integrally mold the seal 48 with the cap. Referring to FIG. 2, at the periphery where the cap sealing surface 48 extends downstream and inward toward axis 42, a corner is formed and the outer edge of the fluid dispenser 26 is placed in this corner.

As the cap 28 is threaded onto the container 20 using threads 34, 36, the downstream side of the cap sealing surface 48 abuts the upstream side of the cap lip 44 to form a fluid tight seal. The cap lip 44 on the distal or downstream edge of the cap 28 abuts the flange 40 on the container to prevent over-tightening and preferably, but optionally also form a redundant seal. As the cap 28 is threadingly tightened on the container 28 the conical cap sealing surface 48 is resiliently urged toward the container lip 46, squeezing and further sealing the periphery of the fluid dispenser 26 between the seal 48 and the cap 28. The fluid dispenser is thus held between the container and the cap, and distributes fluid along axis 42 across at least a substantial portion of a cross section of the container.

Figure 4:
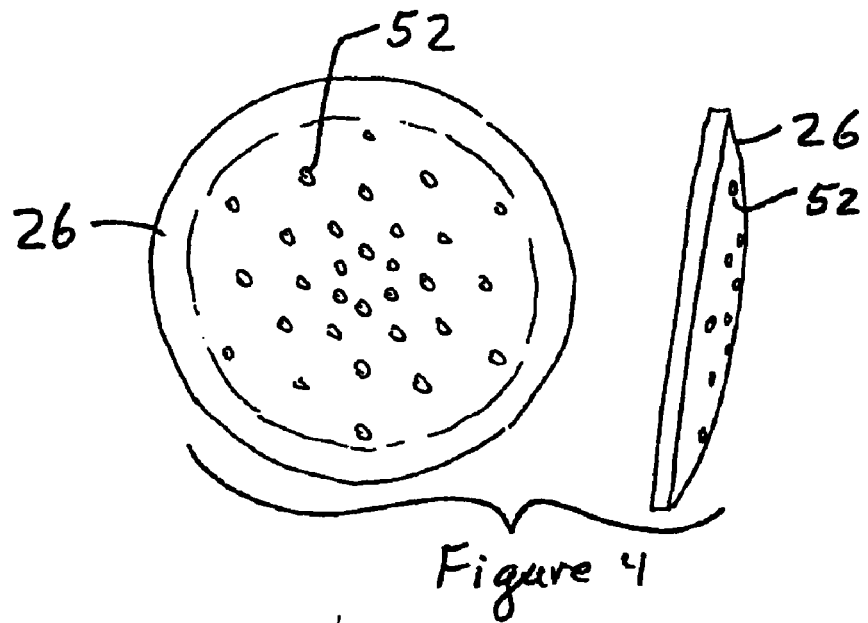
FIG. 4a-b are top and side views, respectively, of the fluid dispenser shown in FIG. 1.

Referring to FIGS. 1, 2 and 4, the fluid dispenser 26 has a containing volume within which the fluid being processed collects and spreads over the cross-section of the container 20 in order to more evenly distribute the fluid over the material in the container. A plurality of holes 52 in the downstream surface of the fluid dispersing device allow the fluid to exit the fluid dispenser 26. Various shaped fluid dispensers 26 could be used, including a container with a flat bottom, or inclined bottoms. As used herein, inclined surfaces include curved surfaces. As the container 20 is preferably, but optionally cylindrical in shape, these shapes result in a cylinder with a flat bottom, or a shallow conical surface or a downwardly curved surface. A flat surface on the dispensing device risks some fluid collecting in the device, and is thus not preferred. Various shaped and sized holes and hole patterns could also be used, with the holes 52 being preferably arranged to distribute the fluid being processed evenly over the cross-sectional area of the container 20. If a curved fluid dispenser 26 is used then the holes 52 may advantageously be larger in diameter as the holes get further from the longitudinal axis.

Still referring to FIGS. 1-2 and 4 the fluid dispenser 26 comprises a circular, domed dish having a plurality of holes 52 extending through the dish. The dish shaped fluid dispenser 26 is preferably, but optionally curved toward the downstream direction so that fluid entering the cap 28 through the inlet port 30 collects in the dish and passes through the holes 52. One hole is preferably located at the lowermost or most downstream portion of the surface to avoid fluid collecting in the fluid dispenser 26. Preferably the lowest opening 52 is on the longitudinal axis 42. A lip or rim of the dispenser is held between the container 20 and the cap 28, and in the preferred embodiment is held by the lip of the container resiliently urging the seal 48 against the rim of the dispensing device 26 against the top 50 of the cap.

The fluid entering the cap 28 through inlet port 30 enters at pressures of about 20-100 psi, and preferably about 50 psi, and at a flow rate of about 10-100 ml/min, although the pressure and flow rate can vary. The pressure and flow rate of the fluid entering the cap 28 and collecting on the fluid dispenser 26 is sufficient that the fluid spreads across the upstream surface of the dish shaped fluid dispenser 26 and squirts through the holes 52 like a showerhead to more evenly distribute the fluid over the cross-section of the container.

Figure 3:
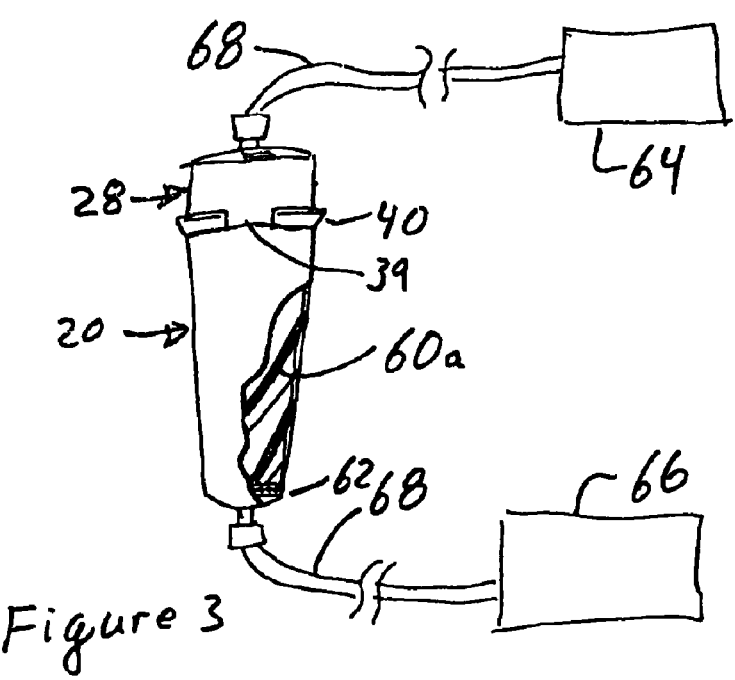
FIG. 3 is a schematic view of the cartridge of FIG. 1 connected to chromatographic equipment.

Referring to FIGS. 1-3, the container 20 is at lest partially filled with a chromatographic packing material 60 selected to suit the fluids being analyzed and the operating pressures and conditions. This is advantageously done by the user just before the cap 28 is locked onto the container 20. Various silica based sorbents are commonly used, and various sorbents 60a, 60b (FIG. 2) or other chromatographically useful materials can be layered by the user to achieve different effects on the fluid being processed. The level of the chromatographic packing material 60 can be varied by the user to leave a predetermined volume inside the container 20, with fluids or other materials being added to fill that predetermined volume.

The dish shaped dispensing device 26 is preferably thin, with a thickness of about 1/16 inch (16 mm) is believed suitable when the dish is made of polypropylene. The thickness and material will vary with the operating pressures and fluids being used. A radius of curvature of about 1-2 inches for the dish shaped dispensing device is believed suitable, and 1.5 inch curvature is used in one embodiment, but other curvatures could be used. The holes 52 are preferably, but optionally all the same diameter and are equally spaced. A diameter of about 0.03 to 0.04 inches (about 7-10 mm) for the holes 52 is believed suitable. The spacing and size of the holes 52 can vary to suit the fluids and pressures being used, and are preferably varied to ensure uniform flow through the dispensing device 26 across the entire cross-section of the container. The dispensing device 26 can be made of materials suitable for the processing of the desired fluid. The fluid dispenser 26 is preferably made of a polymer, such as polyethylene or polypropylene, and preferably of high density polypropylene. Other polymers can be used, although are preferably used that are low cost and suitable for injection molding to form disposable containers and caps. But metal dispensing devices are also believed suitable, such as stainless steel.

Referring to FIGS. 1 and 3, in use a desired amount of filtering media or chromatographic packing material 60, such as a silica sorbent, is placed in the downstream end of the container 20 by the user. Removing a partially secured, and unlocked screw cap 28 allows easy access to place the chromatographic packing material 60 in the container, to adjust the amount of material in the container, to add a different material or sorbent to the container or to adjust the amount of free volume in the container to receive the sample fluid or material or sorbent. A frit 62 can optionally be placed on the upstream and/or downstream end of the chromatographic packing material 60 as desired. The cap 28 and fluid dispenser 26 are then fastened to the container 20 to seal the media 60 inside the container 20. The inlet port 24 can then be connected to a chromatographic fluid source or fluid pressurizing source 64 and the outlet 26 connected to chromatographic processing equipment 66 using tubing 68 which tubing is typically flexible. The cap 28 is preferably not removable from the container 20 once it is installed by the end user and the locks 29 engage the recesses 41. Thus, any adjustment of the chromatographic packing material 60 or other contents of the container 20 is done before the cap 28 is sealingly fastened to the container 28. The fluid to be processed is then passed through the inlet 30, through the fluid dispersing device 26, through the contents of the container 20 (e.g., through chromatographic packing material 60) and out the outlet 24. After use the container 20 and cap 28 can be discarded.

This user access and easy modification of the contents of the cartridge was not previously possible as the containers were welded shut at the factory to ensure they didn't leak under the operating pressures. There is thus advantageously provided a low cost, disposable cartridge made of a polymer which has a threaded, sealed cap on the container. The locking tabs 39 and mating recesses 41 provide locking means on the container and cap for preventing manual removal of the cap. The locking tab 39 forms a member resiliently urged into a recess, and various arrangements of such resiliently engaging parts, such as various forms of spring loaded detents and spring loaded mating members can be devised to form the locking means, especially given the disclosures herein. The seal 48 and lip 46 provide resilient sealing means for sealing the cap to the container when a user places the cap on the container. The sealing means includes numerous other seal types, including one or more O ring seals interposed between abutting portions of the cap 28 and container 20.

There is also provided a method in which a chromatographic packing material 60 is placed in a container either by the manufacturer, or the user, but with the cap not being locked to the container, as by partially threading the cap onto the container but not engaging the locking tabs 39 with the recesses 41. Alternatively, the cap is not placed on the container. The user removes the cap 28 and either alters the prior amount of chromatographic packing material 60, or adds chromatographic packing materials of a different type, or adds further materials or chemicals to affect the fluid being processed by the user in the cartridge or even adds analyte or fluid to be analyzed. The user then places the cap 28 on the container and seals and locks the cap to the container 20. The desired processing is then performed using the cartridge and modified sorbent contained in the cartridge. Given the ability to remove the cap 28 and access the inside of the container 20 immediately before fluid is passed through the container, a variety of process variations can be devised.

The inlet and outlet ports 30, 24, respectively preferably comprise fittings adapted for use in chromatographic applications, and Luer fittings are commonly used. Advantageously the desired fittings at ports 24, 30 are integrally molded with the container 20 and cap 28 to form a unitary construction.

Figure 5:
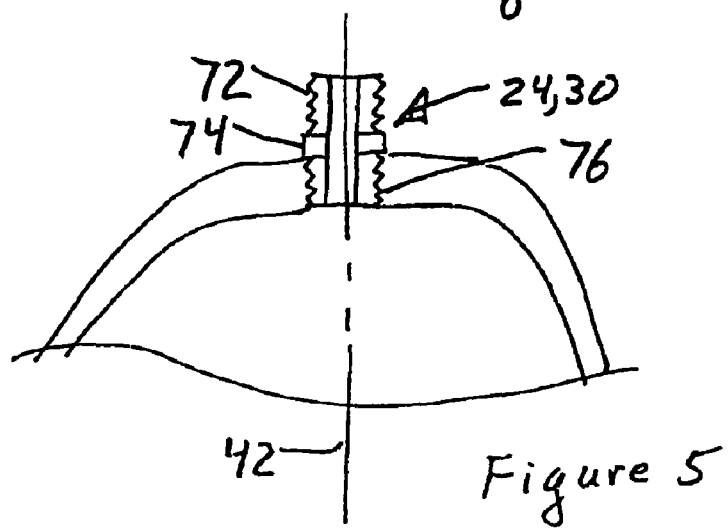
FIG. 5 is a partial sectional view of a further embodiment of inlet and outlet fittings for use with the cartridge of FIG. 1.
Figure 6:
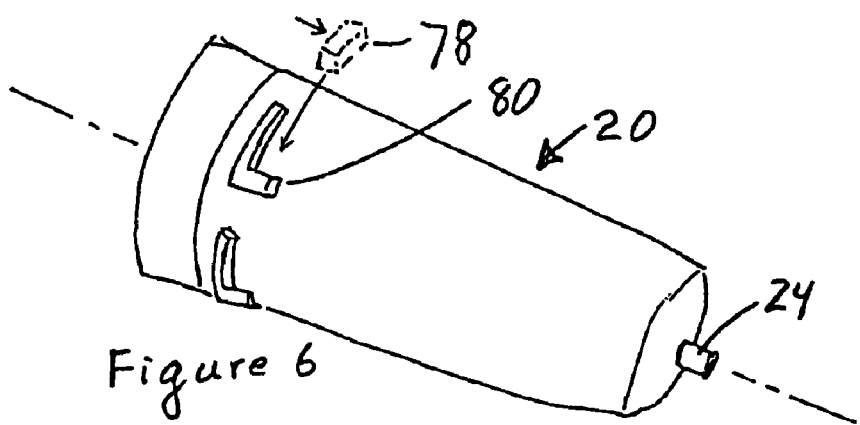
FIG. 6 is a plan view showing a further embodiment of a container and locking mechanism.

Referring to FIG. 5, in a further embodiment the fittings can comprise metal or plastic tubes 72 having external engaging threads 74 adapted for use with chromatographic equipment. A ¼-28 threaded fitting is believed suitable for the engaging threads 74. The tubes 72 can have an opposing end with sealing threads 76 configured to sealingly engage mating threads formed at the location of one or more of the ports 24, 30. The threaded portion of the cap 28 and container 20 may need to be thickened to provide sufficient threaded engagement. The sealing threads 76 preferably form a seal suitable for use up to about 100 psi or higher. Using slightly different thread dimensions or lead angles on the mating threads of the fitting 72 and container or cap can help achieve the desired leak proof seal.

Referring to FIG. 7 a slightly different cap and container are shown in which there are continuous threads 34, 36. There is no flange 40 on the container 20, and the lip on the container is only slightly inclined away from the longitudinal axis 42. The fluid dispenser 26 is held in a corner formed by a slight inward projection of the cap which projection extends toward the axis 42. The fluid dispenser 26 can be snapped into position in the cap 28, and tightening the cap onto the container preferably, but optionally helps further squeeze the periphery of the dispenser 26 between abutting portions of the cap. FIG. 7 shows the top 59 with an annular recess 51 which allows the thickness of the top 50 to remain fairly constant which helps molding of the cap 28. Further, the recess 51 adds flexibility to the sealing surface 48 on the cap 50 and that is believed to enhance the performance of the fluid tight seal which must maintain the seal under flash chromatography and LPLC conditions.

Figure 8:
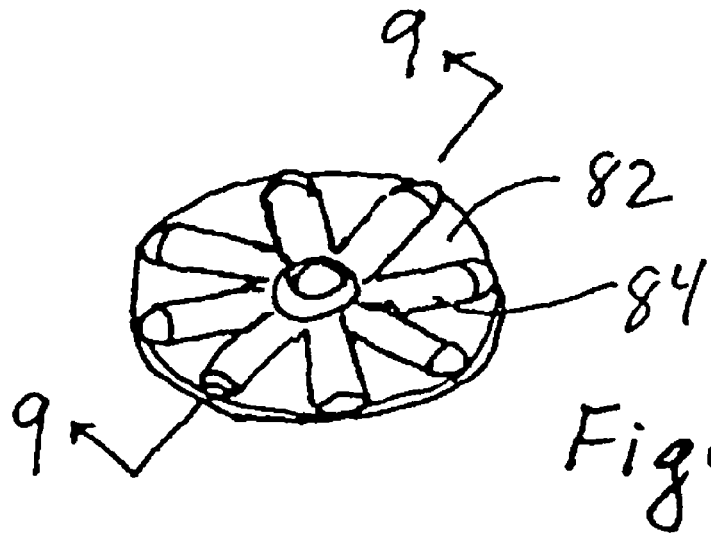
FIG. 8 is a further embodiment of a fluid dispenser.
Figure 9:
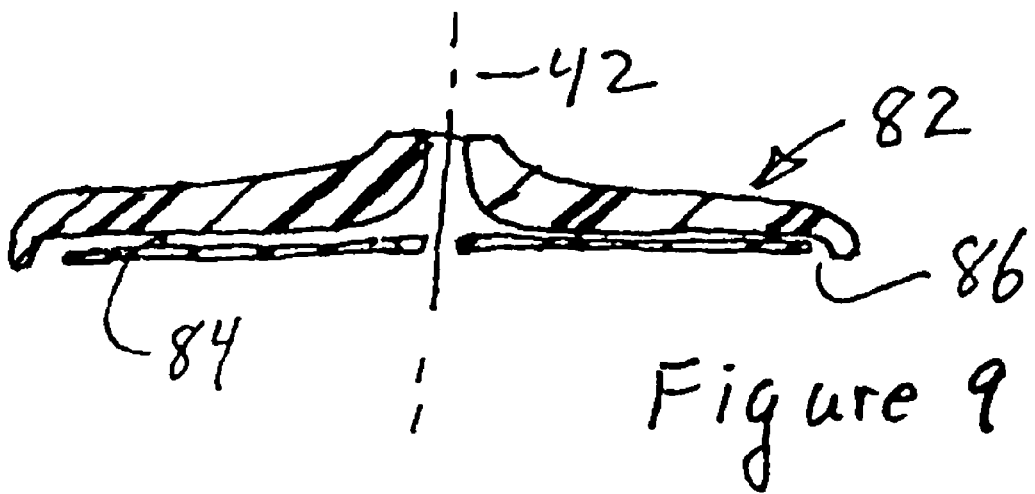
FIG. 9 is a section of the fluid dispenser of FIG. 8 taken along section 9-9 of FIG. 8.

Referring to FIGS. 8-9, a further embodiment of the fluid dispenser 26 is shown which has a generally a disk shaped support for a plurality of radially extending flow channels 84 having openings 86 in fluid communication with inlet 88. Fluid to be analyzed enters through central inlet 88 that is advantageously located on the longitudinal axis 42, and flows across the cross-section of container 20 (FIG. 1) through channels 86 and then out openings 86 onto the packing material. The openings 86 are preferably at the distal end of each channel 86, but could be located at one or more locations along the length of channel 86. This configuration is more difficult to mold than the fluid dispenser of FIG. 1. This embodiment of the fluid dispenser 26 is held between the cap 28 and container 34 as is the prior embodiment of the fluid dispenser. Various ways of holding the fluid dispenser 26 in the desired position will be apparent to one skilled in the art given the disclosures herein, including various clamps, ledges, snap-fits. The various forms of the fluid dispenser 26 comprise means for distributing the fluid to be analyzed over the packing material and over the cross-section of the container 20.

The threads 24, 36 provide means for fastening the cap 28 to the container 20. But the threads represent one specific form of inclined mating surfaces, and other means for fastening the cap to the container include the broader use of inclined mating surfaces. Thus, a lug 78 on one of the cap 28 or container 20 can mate with a bayonet mount 80 on the other of the cap or container to fasten the cap to the container. Placing the recess 41 on a trailing end of an inclined surface on the bayonet could allow the bayonet to also lock the lug into position so as to combine the locking means and the fastening means.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The above description is given by way of example, and not limitation. Given the above disclosure, one skilled in the art could devise variations that are within the scope and spirit of the invention, including various ways of sealing the cap to the container and various process steps that alter the material in the container through which the fluid being analyzed is passed. Further, the various features of this invention can be used alone, or in varying combinations with each other and are not intended to be limited to the specific combination described herein. Thus, the invention is not to be limited by the illustrated embodiments but is to be defined by the following claims when read in the broadest reasonable manner to preserve the validity of the claims.

What is claimed is:

1. A method for low pressure liquid chromatographic analysis of a material using a liquid chromatographic cartridge kit assembled by a user of the kit, said kit including a hollow cylindrical polymer container and a polymer cap with a fluid inlet for attachment to one end of said container by the user to form a chromatographic cartridge, wherein said container includes a fluid outlet at another end thereof and has a chromatographic packing material placed therein before said kit is obtained by the user, said packing material having a surface spaced from said one end of said container to form a predetermined volume between said surface and said cap sufficient to hold a sample for chromatographic analysis when said cap is attached to said container, and said container further includes a threaded portion on an external surface thereof proximate to said one end and said cap comprises a depending skirt having a threaded portion on an internal surface thereof for engaging said threaded portion on said container, the method comprising:

placing the sample in said volume;

thereafter screwing said cap onto said container into a final position by engaging said respective threaded portions to provide a seal between said container and said cap capable of withstanding pressures up to about 100 psi, said seal being formed between (a) an inner surface of said container proximate to said upstream end thereof, said container including an inclined lip portion surrounding said inner surface of said upstream end, and (b) a cap flange disposed for accepting said container between said skirt and said flange with said inclined container lip portion contacting said cap flange to urge said flange inwardly toward said longitudinal axis as said cap is screwed onto said container and into said final position;

attaching a low pressure liquid chromatographic apparatus to said inlet for introducing chromatographic process fluid into said inlet under a pressure up to about 100 psi; and introducing said chromatographic process fluid from said outlet to said low pressure liquid chromatographic apparatus for analysis.

2. A method for low pressure liquid chromatographic analysis as in claim 1, wherein said cap has been screwed onto said container when said kit is obtained by the user, said method further comprising:

removing said cap from said container before placing the sample into said volume; and resealing said cap to said container.

\* \* \* \* \*